United States Patent
Royon-Lebeaud et al.

(10) Patent No.: US 11,298,632 B2
(45) Date of Patent: Apr. 12, 2022

(54) DISTRIBUTION SYSTEM USING MERIDIAN PANELS FOR A SIMULATED MOVING BED SEPARATION METHOD USING N COLUMNS IN SERIES

(71) Applicant: IFP Energies Nouvelles, Rueil-Malmaison (FR)

(72) Inventors: Aude Royon-Lebeaud, Lyons (FR); Frederic Augier, Saint Symphorien d'Ozon (FR)

(73) Assignee: IFP Energies Nouvelles, Springfield (FR)

( * ) Notice: Subject to any disclaimer, the term of this patent is extended or adjusted under 35 U.S.C. 154(b) by 164 days.

(21) Appl. No.: 16/758,885

(22) PCT Filed: Oct. 17, 2018

(86) PCT No.: PCT/EP2018/078434
§ 371 (c)(1),
(2) Date: Apr. 24, 2020

(87) PCT Pub. No.: WO2019/081311
PCT Pub. Date: May 2, 2019

(65) Prior Publication Data
US 2020/0261827 A1    Aug. 20, 2020

(30) Foreign Application Priority Data
Oct. 27, 2017 (FR) ...................................... 1760168

(51) Int. Cl.
*C07C 7/12* (2006.01)
*C07C 7/13* (2006.01)
*C07C 7/00* (2006.01)
*B01D 15/18* (2006.01)

(52) U.S. Cl.
CPC ............ *B01D 15/1842* (2013.01); *C07C 7/12* (2013.01)

(58) Field of Classification Search
None
See application file for complete search history.

(56) References Cited

U.S. PATENT DOCUMENTS

| | | | |
|---|---|---|---|
| 7,582,207 | B2 | 9/2009 | Hotier et al. |
| 8,641,906 | B2 | 2/2014 | Augier |
| 2008/0121586 | A1 | 5/2008 | Hotier et al. |
| 2011/0108145 | A1 | 5/2011 | Augier |

(Continued)

FOREIGN PATENT DOCUMENTS

| | | |
|---|---|---|
| CN | 103285621 A | 9/2013 |
| EP | 1913988 A1 | 4/2008 |
| FR | 2930454 A1 | 10/2009 |

OTHER PUBLICATIONS

International Search Report dated Dec. 3, 2018 issued in corresponding PCT/EP2018/078434 application (2 pages).
English Abstract of CN 103285621 A published Sep. 11, 2013.

*Primary Examiner* — Tam M Nguyen
(74) *Attorney, Agent, or Firm* — Millen, White, Zelano and Branigan, P.C.; Harry Shubin

(57) ABSTRACT

The present invention describes a fluid distribution and collection device of a simulated moving bed separation unit comprising N plates, themselves divided into meridian panels, which device makes it possible to maintain an approximately identical residence time for each portion of fluid.

6 Claims, 4 Drawing Sheets

(56) References Cited

U.S. PATENT DOCUMENTS

| | | | |
|---|---|---|---|
| 2015/0152025 A1* | 6/2015 | Cizeron | ................ B01J 8/1827 |
| | | | 585/324 |
| 2017/0298091 A1* | 10/2017 | Stone | ....................... C07K 1/20 |
| 2018/0296941 A1* | 10/2018 | Augier | .................... C07C 15/02 |
| 2019/0009251 A1* | 1/2019 | Parmentier | ........ B01J 20/28045 |
| 2019/0022654 A1* | 1/2019 | Hammerschmidt | ..... C07K 1/14 |

* cited by examiner

DISTRIBUTION SYSTEM USING MERIDIAN PANELS FOR A SIMULATED MOVING BED SEPARATION METHOD USING N COLUMNS IN SERIES

CONTEXT OF THE INVENTION

The present invention relates to a device for introducing and collecting fluids in the process for separating xylenes in a simulated moving bed (abbreviated to SMB), and the units that use said process, more particularly the units of large diameter (D>4 m), and that have many separation stages with injection or withdrawal of products between two stages.

The device according to the invention has the distinctive feature of adhering to a residence time that is more or less equal for all of the fluid particles entering into the distribution channel, passing through the bed, and being discharged via a collection channel, symmetrical with the distribution channel.

EXAMINATION OF THE PRIOR ART

The current technologies for separation by simulated moving bed (abbreviated to SMB in the remainder of the text) use units which have a certain number of common features:
  a succession of adsorbent beds within which the "pump around" flow flows. This pump around flow generally represents several times the incoming feedstock flow rate (approximately between 1.5 and 6 times).
  systems for injecting the feedstock and the solvent, and for withdrawing effluents referred to as extract and raffinate,
  collection and redistribution systems for passing from one bed to the next bed.

In the processes for separation by simulated moving bed adsorption there are generally a plurality of beds located in one or two adsorption columns Located between each bed are distributor-mixer-extractor or "DME" panels supplied by lines which usually have the shape of "distribution/extraction spiders". Each DME panel located between two consecutive beds is connected to the outside by means of one or two lines or networks leading to a valve that successively places each of the beds in communication with each of the streams entering into or exiting from the adsorption section. This operation is carried out sequentially, and the time at the end of which the initial bed is returned to is referred to as the cycle time, which is an important element of the process.

For example, U.S. Pat. No. 2,985,589 clearly shows that each of the injection or withdrawal networks is connected via a single line to a valve which successively connects the feedstock, the extract, the solvent then the raffinate. This way of proceeding has the drawback of considerably reducing the performance of the process since each stream is thus contaminated by the content of the common line. It is therefore essential to install a rinsing system.

Several patents explain how to carry out these rinsing operations, notably patents FR275188, FR2772634, FR2870751.

The rinsing operations generally prove expensive in regard to investment (additional valve and line), and also in regard to operating cost (yield, productivity).

The "distribution/extraction spiders" constitute obstacles within the adsorbent bed which disturb the flow in the bed. Patent WO 09133254 shows how to minimize the impact of obstacles on the hydrodynamics in the bed.

The article by Augier et al. in 2008 (Separation and Purification Technology 63, pp. 466-474) evaluates the cost of the obstacles.

BRIEF DESCRIPTION OF THE INVENTION

Figure 1:
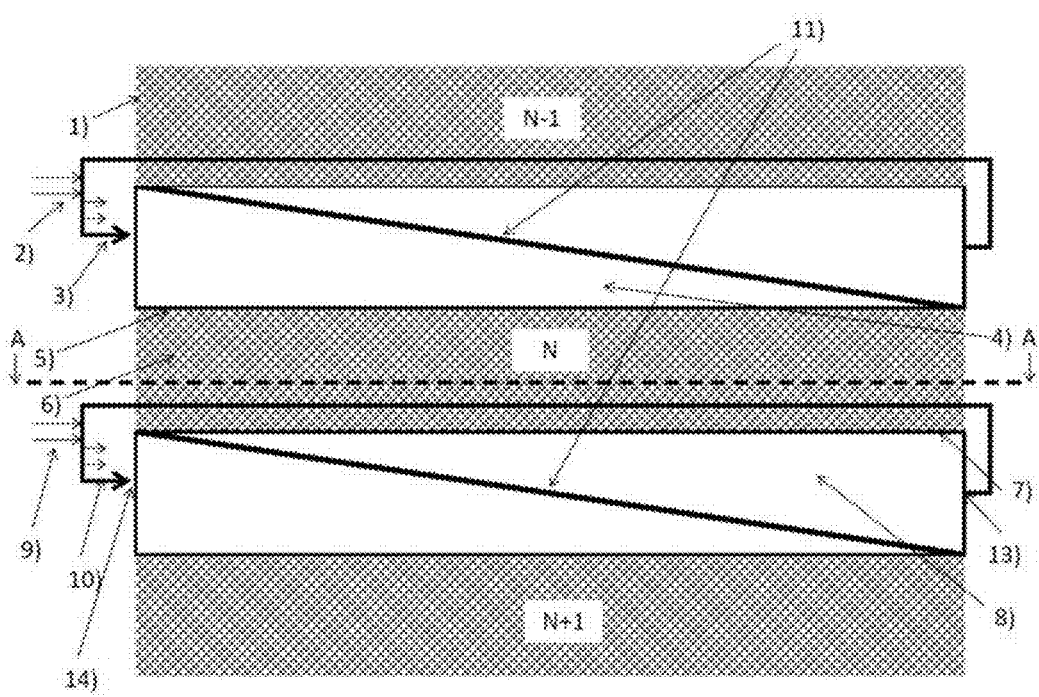
FIG. 1 shows a side view of 3 successive plates, denoted N−1; N and N+1 from top to bottom. It makes it possible to clearly visualize the distribution channel (4) and the collection channel (8), which are symmetrical with respect to one another and are separated by the wall (11), with the return of the fluid from the outlet (7) of the collection channel (8) to the inlet (10) of the distribution channel in the bed N+1.

The present invention may be defined as a distribution and collection system/device for the simulated moving bed separation units with a diameter of greater than 4 meters, preferentially greater than 7 meters, the unit comprising at least one separation column divided into N beds of adsorbent supported by the plate N, each plate N itself being divided into meridian panels, i.e. into panels that are mutually parallel and contiguous so as to ensure complete coverage of the cross section of said bed, and each panel being fed by a distribution channel (4).

The withdrawal of the effluents from said panel takes place via a collection channel (8), the distribution channel and the collection channel surrounding each panel having heights that vary linearly over the entire length of the panel, and being such that the inlet velocity in the bed of each portion of fluid remains the same from the inlet section of the panel to its outlet section of the panel, and that the sum of the heights of the distribution channel and of the collection channel taken at any point of the length of the panel remains constant. For the sake of clarity of the various dimensions of the channels, the length refers to the dimension of the channel corresponding to the distance separating the inlet of the channel from its outlet, the width of the channel refers to the horizontal dimension perpendicular to the length, and the height refers to the vertical dimension perpendicular to the length.

More specifically, the height of the distribution channel decreases linearly from the inlet to the outlet, and the height of the collection channel increases linearly from the inlet to the outlet.

At each abscissa x corresponding to a standard point M on the length of the panel, the sum of the heights of the distribution channel and of the collection channel is constant.

The distribution and collection system according to the invention uses a peripheral duct (10) outside of the column which makes it possible to connect the various collection channels of the plate N to the various distribution plates of the plate N+1, said duct making it possible to carry out injections of feedstock and of solvent and withdrawals of raffinate and of extract.

In a first variant of the distribution and collection system for the SMB separation units according to the invention (represented in FIG. 2), the distribution of the fluids over the various panels of a bed N takes place by successive divisions into two of the stream originating from the duct (10) in order to supply the inlets (14) of two adjacent panels, and the collection of the effluents from the bed N also takes place by combining, in twos, of the outlets (13) of two adjacent panels, which feeds the duct (10) of the bed N+1.

In a second variant of the distribution and collection system for the SMB separation units according to the invention (represented in FIG. 3), the distribution of the fluids over the various panels of a plate N takes place from a distribution manifold (15) which directly supplies the various inlets (14) of each panel, and the collection of the effluents from said bed N takes place in the same manner directly by means of a collection manifold (16) which recovers the effluents from the outlets (13) of each panel.

The present invention also relates to a process using the distribution and collection device according to the invention, in which process the incoming fluid at a plate N is introduced into each panel of said plate N by means of inlet ducts (14), each inlet (14) supplying a distribution channel (4), the height of which is maximum at the inlet and minimum at the outlet of said channel, each portion of fluid supplying a fraction of the granular bed located immediately below the distribution channel, and said fraction of fluid leaving the granular bed in order to enter into the collection channel (8) located immediately below the granular bed, said collection channel having its maximum height at the outlet and its minimum height at the inlet, the outlet effluent then being recovered by the outer peripheral duct (10), and being reintroduced via the inlets (14) of the bed N+1 into the distribution channel of said bed N+1.

The present device applies particularly to the process for separating xylenes in a simulated moving bed operating with a number of beds of between 4 and 24, and preferentially of between 8 and 12.

DETAILED DESCRIPTION OF THE INVENTION

The present invention consists of a device that can be applied to simulated moving bed units, the device making it possible:
to ensure a total collection of the "pump around" stream in order to dispense with rinsing operations;
to minimize the obstacles within the bed. "Pump around" is the terminology used by those skilled in the art to denote the flow circulating in the entire column.

The total collection of the "pump around" stream is an extremely important issue in simulated moving bed units, since it makes it possible to eliminate the rinsing operations.

The technology described in the present invention uses the principle of compensation of the residence times within the collection and distribution zones in order to minimize the variances, i.e. the differences in residence times of the fluids circulating in the unit as a function of the starting point and of the end point of said fluids.

Furthermore, the inter-bed volumes are minimized by working at the same velocity rather than at the same channel height in the collection and distribution zones. The total space requirement of the column is also minimized by stacking the beds. Therefore there is no specific inter-bed volume management.

The flow originating from the bed N−1 (1) is collected in the duct (3).

The injections or withdrawals are carried out by the network of ducts (2).

The distribution channel (4) ensures a uniform distribution of the flow in the bed N, denoted by (6) in FIG. 1, through the grid (5).

The flow is collected by the collection channel (8) through the lower grid (7).

All of the flow is collected in the duct (10) in order to be reinjected into the bed N+1, located immediately below the bed N, after injection or withdrawal via the network (9).

The separation plates (11) separate the collection channel from the distribution channel (4). It is important to ensure the flatness of the separation plate (11) by any means known to a person skilled in the art. The separation plate (11) could for example be firmly attached to the lower and upper grids (5) and (7).

It is also possible to use tie rods extending over the entire width of the panel, joined to beams or plates which delimit said panels over the height of the collection and distribution channels.

The height at the inlet of the distribution channel (4) is defined by a maximum allowable discharge velocity so as not to destabilize the supplying of the bed. Typically, the maximum allowable discharge velocity is between 0.1 and 5 m/s, ideally between 0.5 and 2.5 m/s.

The cross section of the distribution channel (4) decreases linearly in order to guarantee a virtually uniform velocity over the entire length of the channel, equal to this maximum discharge velocity. This constancy of the velocity originates from the fact that the flow rate of fluid is always proportional to the inlet cross section, this being on each inlet cross section of the channel.

The height profile of the distribution channel is therefore linear in order to ensure this proportionality.

The collection channels (8) and distribution channels (4) are complementary in the sense that the distribution channel (4) located immediately above the bed N is associated with the collection channel (8) located immediately below the bed N. The stream leaving the collection channel (8) is then sent to the distribution channel of the bed N+1 by means of the duct (10) which can be seen in FIG. 2.

This duct (10) approximately follows the cylindrical perimeter of the unit in order to be in a position to enter into the distribution channel of the bed N+1. The network is sized so that the maximum discharge velocity does not exceed a certain maximum velocity, general taken between 4 and 6 m/s (for reasons of vibration).

The distributions and collections are organized in meridian panels (12). Meridian panels is understood to mean the fact that the panels are mutually parallel and contiguous, so as to ensure complete coverage of the cross section of the unit. The number of panels covering a cross section of the unit varies between 2 and 12, preferentially between 4 and 8.

The plates are preferably organized in panels of constant cross section. The flow rates are adjusted in order to have the same velocity within the bed.

Figure 2:
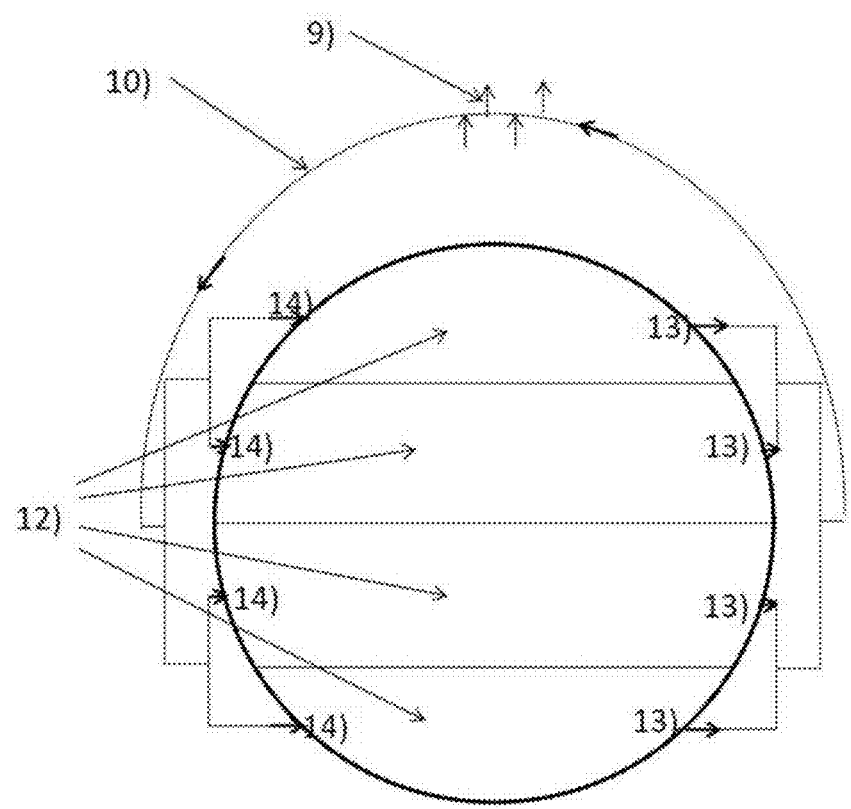
FIG. 2 corresponds to a cross section along the line A-A of FIG. 1. It therefore makes it possible to visualize the plate and the division thereof into meridian panels and also the collection of the fluids by the elements (13) and the distribution thereof by the elements (14). The collection by the elements (13) is combined into two streams, then further combined if necessary. Similarly, the distribution by the elements (14) can be carried out by several divisions into two of the main stream originating from the duct (10).
Figure 3:
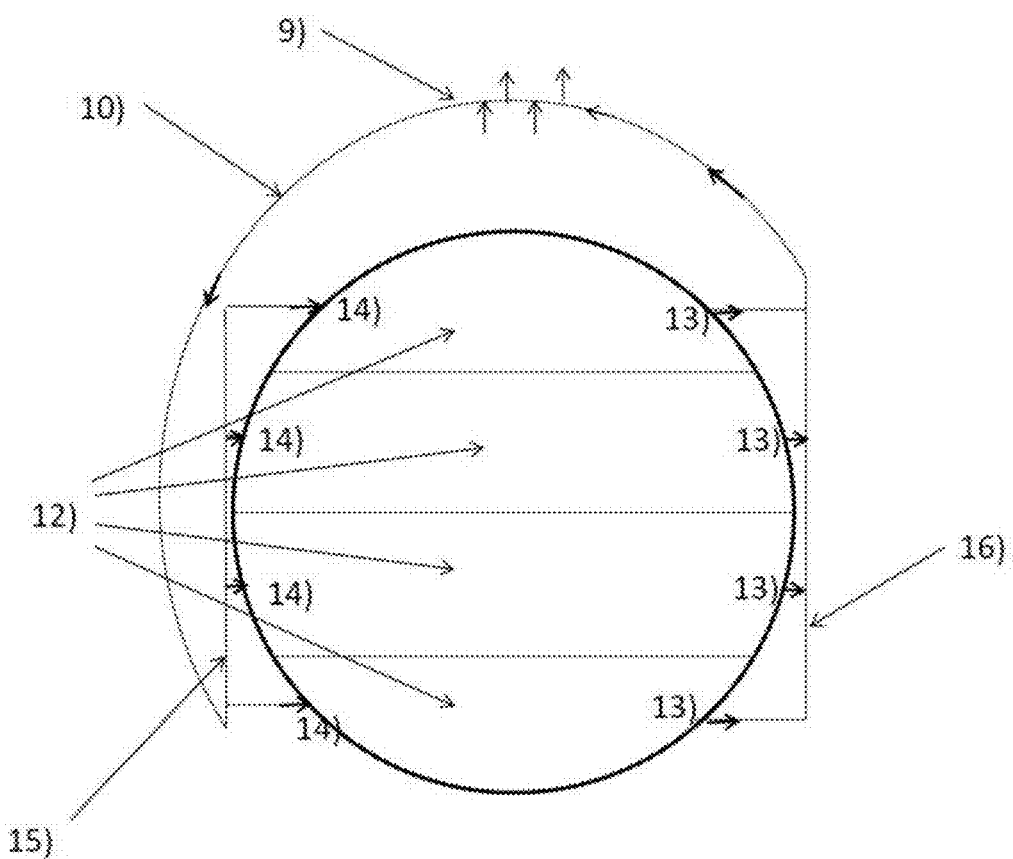
FIG. 3 shows a variant of the distribution/collection system in which all of the streams collected by the ducts (13) on the various panels are taken up in manifold form into a single duct (10) before being redistributed in manifold form into each panel through the ducts (14).

The outer network of ducts (10) is also designed to operate with the same residence time (iso-residence time) both in configuration 1 (FIG. 2), and in configuration 2 (FIG. 3).

Configuration 1 corresponds to a combining, in twos, of the streams leaving each panel.

Configuration 2 corresponds to a direct combining of all of the streams leaving each panel.

The two configurations are represented in FIGS. 2 and 3 which correspond to the cross section along A-A of FIG. 1.

The "network" residence time is used to denote the residence time of a fluid particle from its outlet point of the column, taken to its inlet point into the column, and this being for each of the panels.

It is possible to distinguish between:
the collection side network residence time, which is the residence time of the fluid particle from its outlet point (13) of the column from any panel, to the injection and withdrawal points (9),
the distribution side network residence time which is the residence time of the fluid particle from the injection and withdrawal point (9) to its inlet point (14) into the column toward any panel.

In configuration 1, the network (10) is organized in such a way that all the fluid particles have:
an identical collection side network residence time within the network from the outlet points of each panel (13) to the global injection or withdrawal point (9). That is to say that each fluid particle which leaves the column from any panel takes the same time to travel the distance within the network from its outlet point (13) from the column to the injection/withdrawal point (9).
an identical distribution side network residence time within the network from the global injection or withdrawal point (9) to the inlet points of each panel (14). That is to say that each fluid particle takes the same time to travel the distance within the network from the injection/withdrawal point (9) to its inlet point (14) into the column toward any panel.

The outlets of each panel (13) and the inlets of each panel (14) may be produced by means of 1 to 6 outlet (respectively inlet) points.

The outer network of ducts (10) can have a compensated residence time between collection zone and distribution zone, as shown in FIG. 3 which represents the cross section A-A of FIG. 1 in configuration 2.

In configuration 2, the network residence times are not identical separately between collection side network residence time and distribution side network residence time. In other words, in configuration 2, the fluid is desynchronized between the panels, in addition to the residence time desynchronization inherent to each panel. The desynchronization of the residence times at the inlet of the various panels has no impact on the performance, since it is compensated for by an opposite desynchronization performed by the collection network, owing to the reverse geometry of the supply channels and collection channels.

The outer network (10) is organized in such a way that all the fluid particles have an identical residence time from the outlet point of the panel (13) to the inlet point of the panel (14), but are distributed differently depending on the panel between residence time before the global injection or withdrawal point (9)—collection side network residence time—and residence time after the overall injection or withdrawal point (9) up to the inlet point into the column (14)—distribution side network residence time.

The inlets of each panel (14) may be produced by means of from & to—inlet points.

The outlets of each panel (13) may be produced by means of from 1 to 6 outlet points.

Example According to the Invention

A simulated moving bed adsorption unit (or adsorber) with a diameter of 10 meters is divided into 6 meridian panels of equivalent cross section, and is supplied according to the principle of the invention presented in FIG. 1.

Each bed has a height of 0.77 metre.

The distribution channel (4) has a height of 19 cm at the highest point, i.e. at the inlet of the fluids (14). The height of the channel then decreases linearly with the distance from the inlet wall (14). The collection channel (8) is strictly symmetrical to the distribution channel (4). It has a height that increases from the left side to the right side of the panel in FIG. 1.

Simulations carried out with computational fluid dynamics software FLUENT18.0 show that the principle of the compensation of the residence times between the inlet zone (3) and the outlet zone (13) operates correctly. This satisfactory operation is illustrated by FIG. 4.

Figure 4:
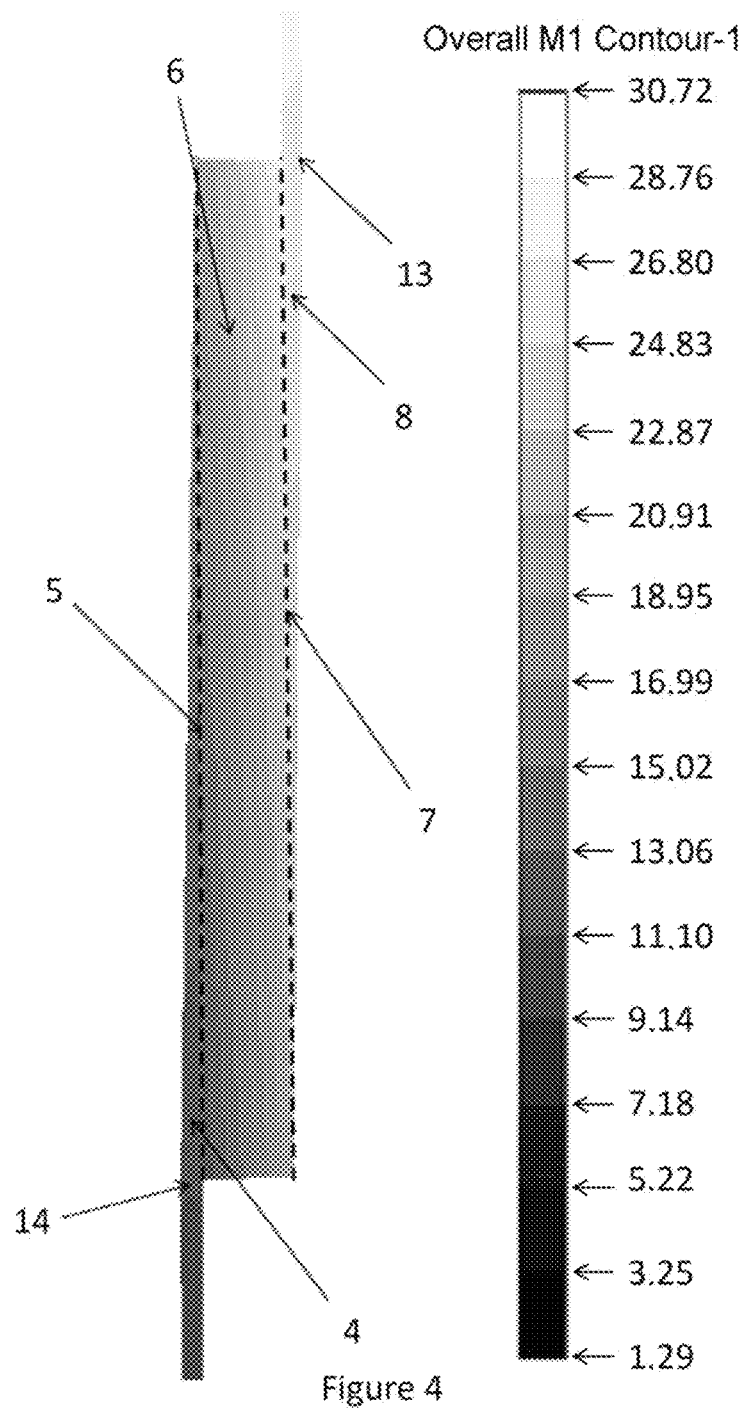
FIG. 4 is a visualization resulting from a numerical simulation. It is a cross-sectional view of a panel, along a cutting plane identical to that of FIG. 1. The inlet into the distribution channel is via the top left edge. The adsorbent bed is the zone between the two grids depicted by a dotted line. The outlet of the collection channel is via the bottom right edge. The grayscale range refers to the average internal age of the fluid in the bed (M1) in seconds.

FIG. 4 is a visualization resulting from this numerical simulation. It is a cross-sectional view of a panel, along a cutting plane of FIG. 1. The inlet (14) into the distribution channel is via the top left edge. The adsorbent bed (6) is the zone between the two grids (5) and (7) depicted by a dotted line. The outlet (13) from the collection channel is via the bottom right edge.

FIG. 4 shows a mapping of the residence times (or internal average age, i.e. the time that has elapsed from the inlet to the outlet of a well marked fluid particle) at any point of the overall system comprising the distribution channel, the adsorbent bed and the collection channel.

The grayscale grid represented at the bottom in the figure indicates the variations in the overall residence time between 0 second represented by black and around 28.3 seconds represented by white. Thus, a fluid particle which has just entered the distribution channel (4) at point (14) has a residence time close to 0 second, and the start of the collection channel is shown in black, then dark gray. Conversely, when a fluid particle leaves the collection channel (7) at the bottom right at point (13), its residence time is around 28.3 seconds, the end of the collection channel being shown in very light gray, then white.

The iso-residence-time lines (lines of the same residence time) are not horizontal in the bed. On the same vertical side within the bed, the fluid particle which has re-entered on the left into the bed, near the inlet to the column, has a very short residence time in the distribution zone, therefore a total residence time that is still higher than the particle that has re-entered into the bed on the right which has a longer residence time in the distribution channel. However, the residence time in the bed of all the fluid particles is identical.

The simulations show that, at the outlet, the differences in residence time generated in the distribution channel (4) have been made up by compensating for them by the variations in residence time in the collection channel (8). The residence time profile is virtually perpendicular to the flow direction in the outlet channel and in the inlet channel.

The calculations show a very low dispersion of the order of 2 $s^2$ which is equivalent to a height equivalent to a theoretical plate of the order of 2 mm. This is an excellent result in terms of uniformity of the residence time.

In the article by Augier et al., 2008, HETP (height equivalent to a theoretical plate) values typical of a technology of an adsorption unit of the order of a centimeter are found.

Reference may be made to FIG. 9, p. 473 of the cited article which represents the HETP for various liquid superficial velocities within the bed. The curve is recalled which corresponds to two configurations of different technologies in the absence of adsorption. The estimated values are between 12 and 20 cm.

The invention therefore has a gain of a ratio of 5 to 10 with respect to the dispersion which can be attributed to the hydrodynamics, which is known to a person skilled in the art to directly affect the performance of the process.

The invention claimed is:

1. A distribution and collection device for the simulated moving bed separation units with a diameter of greater than 4 meters, the unit comprising at least one column divided into N beds of adsorbent, each bed being divided into meridian panels, i.e. into panels that are mutually parallel and contiguous so as to ensure complete coverage of the cross section of said bed, the distribution and collection device comprising distribution channels (4) and collection channels (8), and each panel being fed by a distribution channel (4), and the withdrawal of the effluents from said panel taking place via a collection channel (8), the distribution channel (4) and the collection channel (8) surrounding each panel having heights that vary linearly over the entire length of the panel, and being such that the inlet velocity in the bed of each portion of fluid remains the same from the inlet section of the panel to its outlet section of the panel, and the sum of the heights of the distribution channel and of the collection channel taken at any point of the length of the panel remains constant.

2. The distribution and collection device for simulated moving bed separation units as claimed in claim 1, comprising outer peripheral ducts, wherein the passage of the fluids from plate N to the next plate N+1 takes place by means of a peripheral duct outside of the column and that makes it possible to connect the various collection channels of the plate N to the various distribution plates of the plate N+1, said duct making it possible to carry out injections of feedstock and of solvent and withdrawals of extract and of raffinate.

3. The distribution and collection device for simulated moving bed separation units as claimed in claim 2, wherein the distribution of the fluids over the various panels takes place by successive divisions into two of the stream originating from the outer peripheral duct (10) in order to supply a group of two inlets (14) of adjacent panels, and the collection of the effluents from the bed N also takes place by successive combining, in twos, of the outlets (13) of two adjacent panels, which feeds the outer peripheral duct (10) of the bed N+1.

4. The distribution and collection device for simulated moving bed separation units as claimed in claim 1, comprising distribution manifolds (15) and collection manifolds (16), wherein the distribution of the fluids over the various panels takes place from a distribution manifold (15) which directly supplies the various inlets (14) of each panel, and the collection of the effluents from the bed N takes place in the same manner directly by means of a collection manifold (16) which recovers the effluents from the outlets (13) of each panel.

5. A process using the distribution and collection device as claimed in claim 1, wherein the incoming fluid is introduced into each panel of the plate N by means of inlet ducts (14), each inlet (14) supplying a distribution channel (4), the height of which is maximum at the inlet and minimum at the outlet of said channel, each portion of fluid supplying a fraction of the granular bed located immediately below the distribution channel, and said fraction of fluid leaving the granular bed in order to enter into the collection channel (8) located immediately below the granular bed, said collection channel having its maximum height at the outlet, the outlet effluent then being recovered by the outer peripheral duct (10), and being reintroduced via the inlets (14) of the bed N+1 into the distribution channel of said bed N+1, said process being characterized in that the residence time of each portion of fluid taken from the inlet of the plate N to the outlet of said plate N, is the same for each portion of fluid, and the outer peripheral duct (10) not adding any dispersion to this residence time.

6. An application of the distribution and collection device as claimed in claim 1 to the process for separating xylenes in a simulated moving bed operating with a number of beds of between 4 and 24, and preferentially of between 8 and 12.

* * * * *